(12) United States Patent
Keiji

(10) Patent No.: US 7,799,071 B2
(45) Date of Patent: *Sep. 21, 2010

(54) THREAD FOR VASCULAR STENT AND VASCULAR STENT USING THE THREAD

(75) Inventor: Igaki Keiji, Kyoto (JP)

(73) Assignee: Kabushikikaisha Igaki Iryo Sekkei, Kyoto (JP)

( * ) Notice: Subject to any disclaimer, the term of this patent is extended or adjusted under 35 U.S.C. 154(b) by 84 days.

This patent is subject to a terminal disclaimer.

(21) Appl. No.: 12/052,144

(22) Filed: Mar. 20, 2008

(65) Prior Publication Data

US 2008/0306585 A1    Dec. 11, 2008

Related U.S. Application Data

(63) Continuation of application No. 10/529,194, filed as application No. PCT/JP03/12277 on Sep. 25, 2003, now Pat. No. 7,367,990.

(30) Foreign Application Priority Data

Sep. 25, 2002    (JP) .............................. 2002-279404

(51) Int. Cl.
    *A61F 2/06* (2006.01)
(52) U.S. Cl. ...................................... 623/1.44; 264/211
(58) Field of Classification Search ......... 623/1.11–1.15, 623/1.38–1.48
    See application file for complete search history.

(56) References Cited

U.S. PATENT DOCUMENTS

| 5,653,747 | A  | * | 8/1997  | Dereume | ................... | 623/1.54 |
| 6,652,575 | B2 | * | 11/2003 | Wang    | ................... | 623/1.15 |
| 7,144,422 | B1 | * | 12/2006 | Rao     | ................... | 623/1.42 |

FOREIGN PATENT DOCUMENTS

JP    08-33718    2/1996

* cited by examiner

*Primary Examiner*—Suzette J Gherbi
(74) *Attorney, Agent, or Firm*—K&L Gates LLP

(57) ABSTRACT

A thread for forming a vascular stent implanted in vessels is provided. This thread is formed by melt-spinning a biodegradable polymer. On the surface of the thread, there is formed a layer of a drug-containing biodegradable polymer of the same sort as the biodegradable polymer constituting the thread.

16 Claims, 4 Drawing Sheets

THREAD FOR VASCULAR STENT AND VASCULAR STENT USING THE THREAD

CROSS REFERENCE TO RELATED APPLICATIONS

The present application is a continuation of Ser. No. 10/529,194 filed on Apr. 21, 2005 which was the National Stage of International Application No. PCT/JP03/1227 filed on Sep. 25, 2003 and claims priority to Japanese Patent Application No. 2002-279404, filed on Sep. 25, 2002, the disclosure of which in its entirety is incorporated by reference herein.

BACKGROUND

The present invention relates to a thread for forming a stent for vessels, implanted within vessels of a living body, such as lymph vessels, bile ducts or ureter, for maintaining a patency state of the lumen of the vessels, and to a stent for vessels employing the thread.

In angioplasty, mechanical techniques, such as balloon dilation technique or stent implanting technique, tend to injure blood vessels. In a site of lesion of the blood vessels, acute coronary occlusion, caused by thrombosis, or re-stenosis, caused by intimal hyperplasia of the blood vessel, as a curative reaction of the wall of the blood vessel, occurs frequently.

In acute coronary occlusion, thrombosis plays some role. For possible prevention, antithrornbotic therapy by systemic administration of drugs via veins is customarily used.

On the other hand, re-stenosis is induced by excess hyperplasia of cells.

Currently, researches into drugs for suppressing hyperplasia of cells are going on briskly, and several drugs have been found as giving acceptable results.

For deriving favorable results of these pharmaceuticals, it is necessary to administer the drugs at/in a high concentration or in a large quantity. It has, however, been indicated that side effects tend to be produced by such administration.

Recently, a local drug delivery system (LDDS) has come to be used as a safe and efficacious method for possible prevention of acute coronary occlusion or re-stenosis. In this LDDS, a stent is stirring up notice as a member for transporting the drug to a target site of the blood vessel. With the LDDS, employing the stent, local administration of the drug becomes possible by implanting the stent, carrying the drug, in a target site in the blood vessel. The stent can be implanted in a target site in the blood vessel, without obstructing the blood flow, for a prolonged time, and hence can be used as the LDDS which may produce a sufficient pharmaceutical effect for a prolonged period of time.

Meanwhile, the majority of the stents for blood vessels, used at present for clinical purposes, are made of metal. With metal, the drug cannot be mixed into the material, such that the drug can be applied only to its surface. Among a variety of methods for depositing the drug to the metal stent, there are a coating method and a bonding method, as disclosed in the Japanese Laid-Open Patent Publication H-8-33718. When the drug is deposited on the surface of the metal stent by the coating method or the bonding method, there is raised a problem that the drug itself may peel off from the stent surface. Furthermore, it is difficult to deposit an amount of the drug sufficient to derive the pharmaceutical effect. In addition, since the metal stent, implanted in the blood vessel, remains permanently as a foreign substance, there is a possibility that re-stenosis may be produced in the stent implant site of the blood vessel.

With the LADS, it is necessary to control the content of the drug, the amount of drug release per unit time and the time period of drug release. In order to take precautions against acute coronary occlusion or re-stenosis by the LDDS more effectively, such control is desirable in which the effective concentration of the drug in the target blood vessel site may be maintained and in which the drug may be released for a predetermined period to the blood vessel wall and into the blood.

SUMMARY

The present invention relates to a thread for forming a stent for vessels, implanted within vessels of a living body, such as lymph vessels, bile ducts or ureter, for maintaining a patency state of the lumen of the vessels, and to a stent for vessels employing the thread.

The present invention provides in an embodiment a thread for forming a stent for vessels, and a stent for vessels, in which the drug can be reliably retained to implant in the vessel, such as blood vessel.

The present invention provides in an embodiment a thread for forming a stent for vessels, and a stent for vessels, in which the drug can be released into the body of for a prolonged period of time.

The present invention provides in an embodiment a thread for forming a stent for vessels, and a stent for vessels, in which it is possible to control the drug content, the amount of drug release per unit time, and the time period for drug release.

The present invention provides in an embodiment a thread for forming a stent for vessels, which thread is degraded in vivo after or in the course of drug release without being left as a foreign substance in the living body, and a stent for vessels.

The present invention in an embodiment is directed to a thread for forming a stent for vessels introduced and implanted in vessels, such as blood vessels, in a living body, and comprises a thread formed on melt-spinning a biodegradable polymer and a layer of a biodegradable polymer containing a drug and which is of the same sort as the biodegradable polymer constituting the thread. A biodegradable polymer, in which to contain the drug, is dissolved on being mixed with a solvent, to yield a solution. A drug is mixed or dissolved in this solution of the biodegradable polymer. The solution of the biodegradable polymer, into which the drug is mixed or dissolved, is coated on the thread surface to constitute the drug-containing layer.

The biodegradable polymer, constituting the drug-containing layer, is of the same sort as the biodegradable polymer constituting the thread, and hence is deposited on the thread surface with superior tight adhesive properties. In addition, since the biodegradable polymer constituting the drug-containing layer, is of the same sort as the biodegradable polymer constituting the thread, it may be considered that the two polymers are degraded in vivo with substantially the same speed.

The biodegradable polymer constituting the thread is e.g. an aliphatic polyester. The aliphatic polyester may be enumerated by poly (a-hydroxy acid), such as polyglycolic acid or poly-Lactic acid, and poly(ce-hydroxyalkanoates), such as poly-e-caprolactone. Hence, this sort of the aliphatic polyester is also used as the biodegradable polymer constituting the drug-containing layer.

The thread for the stent for vessels, according to the present invention, may be a monofilament, obtained on melt-spinning a biodegradable polymer. It may also be a multifilament, obtained in the same manner.

As the drug contained in the biodegradable polymer, deposited on the thread surface, such drug exhibiting antithrombotic effect and/or intimal hyperplasia suppressing effect, may be used. The drug exhibiting the intimal hyperplasia suppressing effect may be an immunosuppressive agent or an anticancer agent. An example of the drug exhibiting the intimal hyperplasia suppressing effect is Tranilast [1V-(3,4-dimethoxycinnamoyl)anthranilic acid]. The immunosuppressive agent used may be rapamycin (Sirolimus), while the anticancer agent used may be taxel (Paclitaxel).

In the thread for a stent for vessels according to the present invention, a second layer, formed only of the biodegradable polymer of the same sort as the biodegradable polymer, constituting the thread, is deposited on a first layer of the drug-containing biodegradable polymer. By providing the second layer, formed only of the biodegradable polymer, on the drug-containing first layer, it becomes possible to suppress the time period of release of the drug contained in the first layer, by way of extending the drug release time duration.

In another thread for a stent for vessels, according to the present invention, a drug is mixed into a biodegradable polymer, on the surface of which is formed a layer of a biodegradable polymer of the same sort as the drug-containing biodegradable polymer constituting the thread.

As the drug contained in the thread provided with the drug-containing layer, such a drug exhibiting the antithrombotic effect and/or intunal hyperplasia suppressing effect, similar to that exhibited by the drug contained in the drug-containing layer, may be used.

The drug-containing layer, formed on the thread surface, is formed by coating the thread surface with a biodegradable polymer solution, in which the drug has been mixed or dissolved, as described above.

With the thread for a stent for vessels, containing the drug, the second layer of a biodegradable polymer of the same sort as the biodegradable polymer, constituting the thread, may be formed on the drug-containing first layer of the biodegradable polymer. This second layer is formed on coating the first layer with the solution of the biodegradable polymer.

The present invention provides a stent for vessels formed using above-described threads for a stent for vessels. The stent for vessels is formed by the threads for a stent for vessels being wound to a tube as each of the threads is bent in a zigzag design and is enlarged or contracted in diameter with the bends of the threads as displacing portions.

With the thread constituting the main stent body, obtained on melt-spinning a biodegradable polymer with a screw extruder and on drawing the resulting product, a monofilament may be used. A multifilament, obtained in the same manner, may also be used.

Since the stent for vessels, according to the present invention, is formed using a thread for a stent for vessels, provided with a drug-containing layer on the thread surface with good adhesive properties thereto, the drug is reliably delivered to and implanted in a target site in a vessel, without peeling off from the stent in the course of insertion into the vessel.

Since the stent for vessels according to the present invention is formed using the thread of the biodegradable polymer, it does not remain as a foreign substance in the living body and it is absorbed after a certain period of time.

With the stent for vessels, according to the present invention, a biodegradable polymer layer may be formed on the surface of the main stent body unit, formed using the thread for a stent for vessels, by coating the surface with a solution of the biodegradable polymer of the same sort as the material constituting the thread.

By providing the biodegradable polymer layer on the surface of the main stent body, in this manner, it is possible to suppress release of the drug contained in the drug-containing layer to extend the drug release time duration.

Additional features and advantages are described herein, and will be apparent from, the following Detailed Description and the figures.

DETAILED DESCRIPTION

Figure 1:
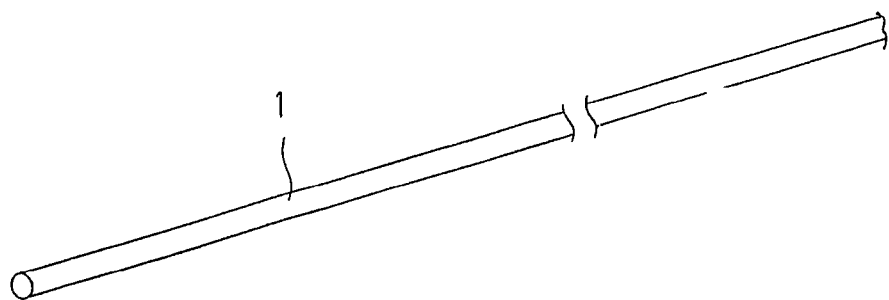
FIG. 1 is a perspective view showing a thread making up the thread for the stent for vessels according to the present invention.

The present invention relates to a thread for forming a stent for vessels, implanted within vessels of a living body, such as lymph vessels, bile ducts or ureter, for maintaining a patency state of the lumen of the vessels, and to a stent for vessels employing the thread.

Referring to the drawings, a thread for a stent for vessels, and a stent for vessels, employing the thread, are explained in detail.

The thread according to the present invention is used for forming a stent for vessels, in particular a stent for blood vessels, used as it is inserted into the blood vessels, such as a coronary artery.

The thread used for forming a stent for vessels, according to the present invention, is formed of a biodegradable polymer which, when implanted in a living body, such as a human body, does not affect the living body. As this biodegradable polymer, an aliphatic polyester is used. Specified examples of the aliphatic polyester include poly (a-hydroxy) acid, such as polyglycolic acid or polylactic acid, and poly(co-hydroxyalkanoates), such as poly-caprolactam.

The thread formed of this sort of the biodegradable polymer may be spun using a screw extruder. For spinning the thread by a screw extruder, pellets of the biodegradable polymer are first charged into a hopper of the screw extruder, and are compressed and melted, within a cylinder, as the pellets are heated to a temperature in the vicinity of a melting point Tm or to a temperature not lower than the melting point and not higher than a thermal decomposition temperature. Within the cylinder, is rotated a screw on the outer periphery of which has been formed a spiral groove. The biodegradable polymer, melted in the cylinder, is extruded from a nozzle, set to a temperature not lower than the glass transition temperature Tg. The linear biodegradable polymer, extruded from the nozzle, is taken up with a take-up device. This linear biodegradable polymer is further drawn when or after it is taken up with the take-up device, to form a thread as a base material for a thread for a stent for vessels according to the present invention.

The thread 1, as the base material for the thread for a stent for vessels, formed according to the present invention, is made up of a continuous monofilament, as shown in FIG. 1.

Figure 2:
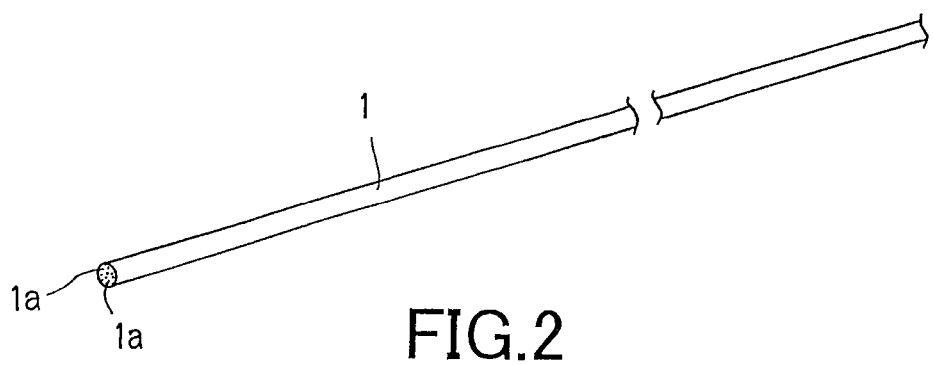
FIG. 2 is a perspective view showing another embodiment of the thread for a stent for vessels according to the present invention.

The thread 1, as the base material for the thread for a stent for vessels, according to the present invention, may be formed not only of a monofilament, but also of a multifilament, composed of plural monofilaments 1a, unified together, as shown in FIG. 2.

The thread 1 may not only be circular but also a flattened in a cross-sectional shape.

Figure 3:
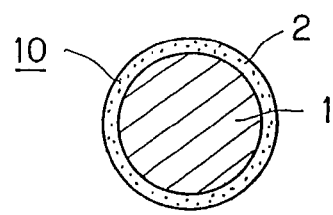
FIG. 3 is a cross-sectional view showing the thread for a stent for vessels according to the present invention.

A thread 10 for a stent for vessels, according to the present invention, is formed from the thread 1, obtained on spinning the above-described biodegradable polymer, as the base material, as shown in FIG. 3.

On the surface of the thread 1, as the base material, there is provided a drug-containing layer 2, as a first layer of a drug-containing biodegradable polymer, as shown in FIG. 3. The drug-containing layer 2 is formed by coating the surface of the thread 1 with a solution obtained on mixing a drug in a biodegradable polymer dissolved with a solvent.

The biodegradable polymer, forming the drug-containing layer 2, is of the same sort of polymer as the biodegradable polymer forming the thread 1. In case the thread 1 is formed of poly-L-lactic acid (PLLA), the biodegradable polymer, forming the drug-containing layer 2, is formed of the same sort of polymer, that is, poly-L-lactic acid (PLLA). The same sort of the biodegradable polymer means the biodegradable polymer which has the same molecular branch and which may differ in molecular weight. For example, the thread 1 may be formed of a high molecular weight poly-L-lactic acid (PLLA), while the drug-containing layer 2 may be formed of poly-L-lactic acid (PLLA) lower in molecular weight than the poly-L-lactic acid (PLLA) of the thread 1.

As the drug contained in the drug-containing layer 2, such a drug exhibiting an antithrombotic effect and/or an intimal hyperplasia suppressing effect may be used. As the drug exhibiting the intimal hyperplasia suppressing effect, an immunosuppressive agent or an anticancer agent may be used. As the drug having the intimal hyperplasia suppressing effect, Tranilast [N-(3,4-dimethoxy cinnamoyl)anthranilic acid] may be used. As the immunosuppressive agent and the anticancer agent, Lapamycin (Sirolimus) and taxel (Pacilt-axel) may be used, respectively.

The solution forming the drug-containing layer 2 is prepared by heating and dissolving pellets of the biodegradable polymer, as a solvent is added thereto, and charging a drug into the dissolved biodegradable polymer.

If poly-L-lactic acid (PLLA) is used as the biodegradable polymer, 1,4-dioxane, used as a solvent, is added to pellets of poly-L-lactic acid (PLLA), and stirred for dissolution, as the reaction system is heated to approximately 90° C. A drug, such as Tranilast powders, is added to the dissolved biodegradable polymer and stirred to produce a drug-containing solution.

Meanwhile, if poly-L-lactic acid (PLLA) is used as a biodegradable polymer, dichloromethane is desirably used.

The drug-containing solution is coated on the surface of the thread 1, using a coating means, to form the drug-containing layer 2.

The thread 1, coated with the drug-containing solution, is rinsed at the outset to remove impurities, such as dust and dirt, affixed to its surface.

The thread 1 is rinsed with ethanol and distilled water. First, the thread 1 is charged into a rinse tank, charged with ethanol, for rinsing. The thread 1, rinsed with ethanol, is charged into a rinse tank, charged with distilled water, for rinsing. The thread 1, thus rinsed, is then dried and coated with the drug-containing solution.

The drug-containing solution, constituting the drug-containing layer 2, has dissolved therein the same sort of the material as the biodegradable polymer constituting the thread 1, on which the solution is coated, and hence is deposited to the thread 1 with satisfactory adhesive properties. The drug-containing layer 2, formed using this solution, is unified to and deposited on the surface of the thread 1 in a manner free from peeling or removal. Hence, the drug contained in the drug-containing layer 2 is carried on the surface of the thread 1 in a manner free from peeling or removal.

By forming the stent for vessels, using the thread 10 for a stent for vessels, in which the drug-containing layer 2 is carried on the surface of the thread 1 in a manner free from peeling or removal, it becomes possible to administer the drug positively to a desired site in the living body.

With the thread 10 for a stent for vessels, the amount of drug release per unit time may be varied by changing the amount of the drug contained in the drug-containing layer 2.

Figure 4:
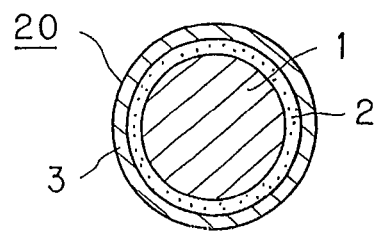
FIG. 4 is a cross-sectional view showing another embodiment of the thread for a stent for vessels according to the present invention.

With a thread for a stent for vessels 20, according to the present invention, a second layer 3, formed only of the biodegradable polymer of the same sort as the biodegradable polymer constituting the thread 1, may be additionally deposited on the drug-containing layer 2, operating as a first layer, as shown in FIG. 4.

The second layer 3 is formed of the same sort of the biodegradable polymer, forming the thread 1, so that, in case the thread 1 is formed by poly-L-lactic acid, the second layer is formed of the same sort of poly-L-lactic acid. That is, the second layer 3 is formed of poly-L-lactic acid (PLLA) which is the same as the thread 1, or of poly-L-lactic acid (PLLA) lower in molecular weight than poly-L-lactic acid constituting the thread 1.

The second layer 3 is formed by coating on the drug-containing layer 2 with a solution obtained on dissolving pellets of a biodegradable polymer in a solvent added thereto under heating.

In case poly-L-lactic acid is used as the biodegradable polymer, forming the second layer 3, such a solution is used, which is obtained on mixing 1,4-dioxane, as a solvent, to pellets of poly-L-lactic acid, and on stirring the resulting reaction mass under heating to approximately 90° C. for dissolution. In this case, dichloromethane may again be used as a solvent in order to obtain a biodegradable polymer solution employing poly-L-lactic acid.

After the drug-containing layer 2 is dried, the biodegradable polymer solution, forming the second layer 3, is applied on this drug-containing layer 2.

The thread 1, on the drug-containing layer 2 of which has been deposited the biodegradable polymer solution, is then completely dried to give a thread for the stent for vessels 20, composed of the drug-containing layer 2 and the second layer 3, formed only of the biodegradable polymer, sequentially layered on the thread 1 as shown in FIG. 4.

With the thread for a stent for vessels, obtained on depositing, on the drug-containing layer 2, the second layer 3, formed only of the biodegradable polymer of the same sort as that of the thread 1, it is possible to control the quantity and time period of release of the drug contained in the drug-containing layer 2.

That is, by constituting the second layer 3, formed only of the biodegradable polymer, on the drug-containing layer 2, it becomes possible to suppress release of the drug contained in the drug-containing layer 2, while it also becomes possible to extend the time period of release of the drug contained in the drug-containing layer 2.

The time duration of release of the drug contained in the drug-containing layer 2 becomes possible by changing the thickness of the second layer 3, that is, the coating thickness of the biodegradable polymer solution making up the second layer 3.

Although the thread constituting the thread for the stent for the vessels, according to the present invention, is formed only of the biodegradable polymer, it is also possible to add the drug to this thread.

Figure 5:
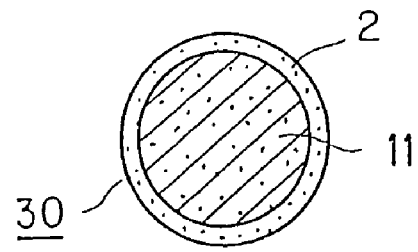
FIG. 5 is a cross-sectional view showing still another embodiment of the thread for a stent for vessels according to the present invention.

An example of the thread for a stent for vessels 30, comprised of a thread 11 containing the drug, is shown in FIG. 5.

The drug-containing thread 11, forming the thread for a stent for vessels 30, shown in FIG. 5, is formed by charging the drug into the hopper, along with pellets, formed of a biodegradable polymer, as the material constituting the thread 1, at the time of spinning on the screw extruder. The pellets of the biodegradable polymer, charged into the hopper along with the drug, are compressed and melted, within a cylinder, as the pellets are heated to a temperature in the vicinity of the melting point Tm or to a temperature not lower than the melting point and not higher than the thermal decomposition temperature. Within the cylinder is rotated a screw on the outer periphery of which has been formed a spiral groove. At this time, the drug is melted and mixed into the melted biodegradable polymer. The biodegradable polymer, melted in the cylinder, and mixed with the drug, is extruded from a nozzle, set to a temperature not lower than the glass transition temperature Tg, and is spun as the thread 11, comingled with the drug, as it is taken up with a take-up device.

As the material of the biodegradable polymer, constituting the thread 11, such a material, the melting point of which is not injurious to the drug, is used. In case Tranilast is used as the drug, the biodegradable polymer, melting at a temperature not higher than 220° C., specifically, poly-L-lactic acid (PLLA), melting at a temperature not higher than $220^2$ C, is used.

The drug-containing layer 2, in the surface region of which is contained the drug, is provided to the surface of the thread 11, containing the drug, as in the case of the above-described thread 1 formed only of the biodegradable polymer, to form the thread for a stent for vessels 30.

As the drug contained in the thread 11 and in the drug-containing layer 2, in this thread for a stent for vessels 30, such a drug exhibiting an antithrombotic effect and/or an intimal hyperplasia suppressing effect, is used. As the drug exhibiting intimal hyperplasia suppressing effect, immunosuppressive agent or anti-tumor drugs may be used. The drug contained in the thread 11 may differ in pharmaceutical efficacy or drug type from the drug contained in the drug-containing layer 2. For example, a drug exhibiting the antithrombotic effect may be contained in one of the thread and the drug-containing layer, while a drug exhibiting intimal hyperplasia suppressing effect may be contained in the other of the thread and the drug-containing layer. Specifically, a drug exhibiting the antithrombotic effect may be contained in the drug-containing layer 2, whilst a drug exhibiting intimal hyperplasia suppressing effect may be contained in the thread 1.

With use of the drug-containing thread 11, it may be expected to release the drug for an extended period of time.

Figure 6:
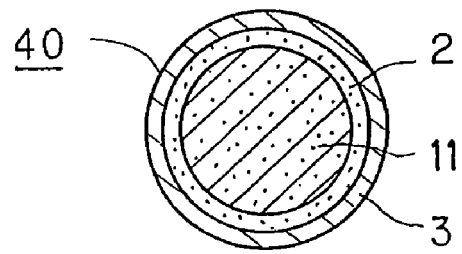
FIG. 6 is a cross-sectional view showing yet another embodiment of the thread for a stent for vessels according to the present invention.

In the thread for a stent for vessels, comprised of the drug-containing thread 11, the second layer 3, formed only of the biodegradable polymer of the same sort as the biodegradable polymer constituting the thread 11, may be deposited on the surface of the thread 11, as shown in FIG. 6. With a thread for a stent for vessels 40, shown in FIG. 6, the second layer 3 is formed of the same sort of the biodegradable polymer as that of the thread 11, so that, if the thread 1 is formed of poly-L-lactic acid (PLLA), the second layer is formed of the same sort of poly-L-lactic acid (PLLA). That is, the second layer 3 is formed of poly-L-lactic acid (PLLA) which is of the same sort as the material of the thread 1, or of poly-L-lactic acid (PLLA) lower in molecular weight than poly-L-lactic acid (PLLA) forming the thread 1.

The second layer 3 is formed by coating, on the drug-containing layer 2, the solution obtained on dissolving pellets of the biodegradable polymer in a solvent added thereto under heating, as described above.

The threads for a stent for vessels, according to the present invention, described above, are used for forming a stent for vessels, used on being introduced into blood vessels, such as coronary artery of the living body.

An example of a stent for vessels, formed using a thread for a stent for vessels, according to the present invention, is hereinafter explained in detail.

The stent for vessels may use a thread for a stent for vessels, comprised of a thread formed only of a biodegradable polymer, or a thread for a stent for vessels, comprised of a thread containing a drug. In the following, such a case in which the thread for a stent for vessels 10, comprised of the thread 1 formed only of the biodegradable polymer, is taken as an example for explanation.

A stent for vessels 21, according to the present invention, is constituted by forming the thread for a stent for vessels 10, described above, into a tube, as shown in FIG. 7.

Figure 8:
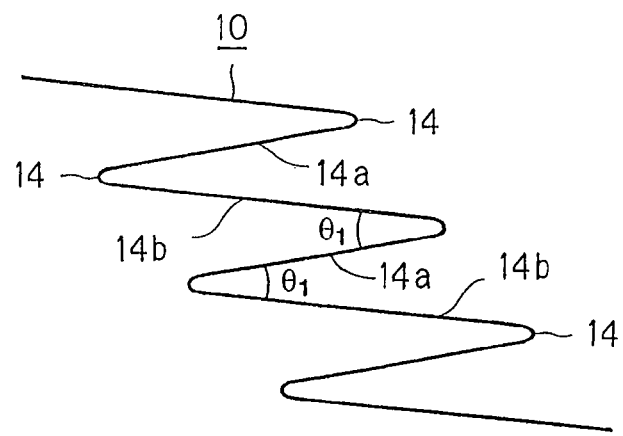
FIG. 8 is a plan view showing the bent state of a thread for a stent for vessels making up a main stent body unit.
Figure 9:
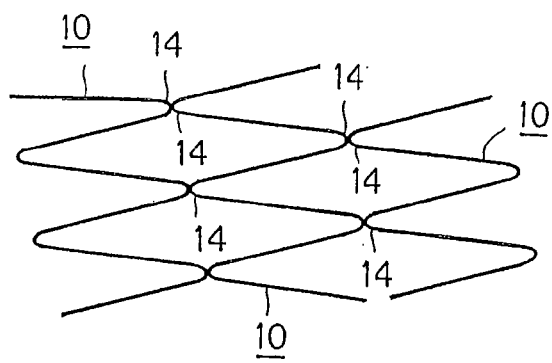
FIG. 9 is a plan view showing a portion of the main stent body unit to an enlarged scale.

The thread for a stent for vessels 10, formed as explained above, is bent in a zig-zag design in concatenated vee shapes and wound spirally to constitute a tubular main body portion of the main stent body 13 as shown in FIG. 8. A spirally wound shape of the thread for a stent for vessels 10 is obtained with a side of a bend 14 of the vee shape as a short portion 14a and with its opposite side as a long portion 14b. By setting the lengths of the short portion 14a and the long portion 14b between the bends 14 so as to be approximately equal to each other, the apices of the neighbouring bends 14 are contacted with each other, as shown in FIG. 9. Part or all of the apices of the contacted bends 14 are bonded to one another. The thread for a stent for vessels 10 of the main body portion of the main stent body 13 is positively maintained in the state of keeping the tubular shape by bonding the apices of the bends 14 contacting with each other.

Figure 7:
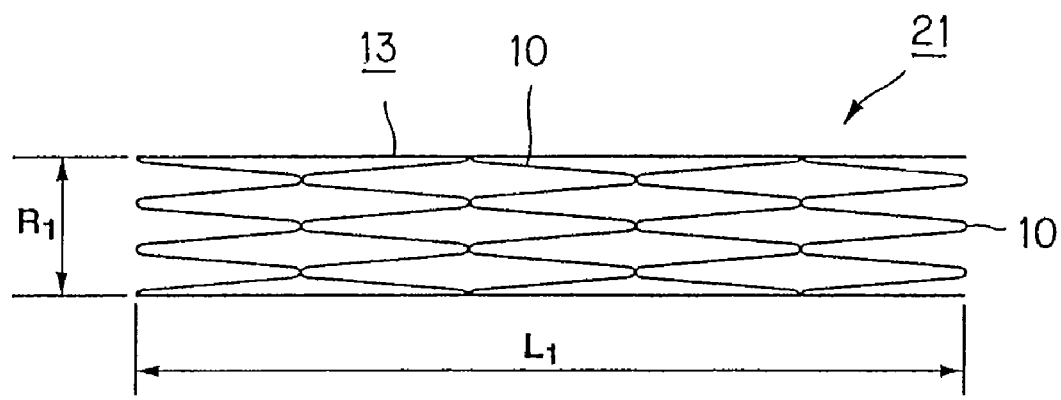
FIG. 7 is a plan view showing a stent for vessels according to the present invention.
Figure 10:
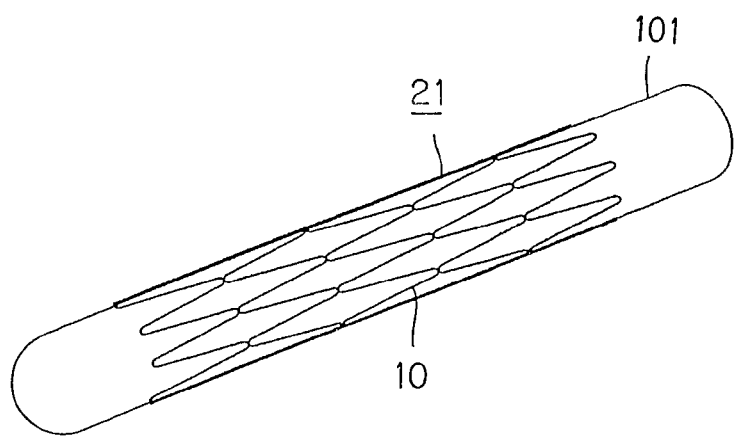
FIG. 10 is a perspective view showing the state of imparting shape memory to the stent for vessels.
Figure 11:
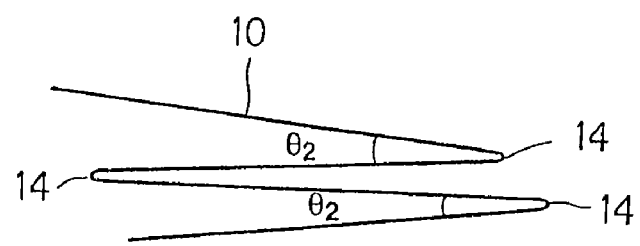
FIG. 11 is a plan view showing the bent state of a thread for a stent for vessels when the stent for vessels is contracted in diameter.

The stent 21, constituted using the tubular main body portion of the main stent body 13, is shape-memorized to the size with which it is implanted in the blood vessel. For realizing this shape memory, as shown in FIG. 10, the stent 21 is equipped on a shaft-like mold frame 101 sized to maintain the size of the stent 21 implanted in the vessel of the living body, and is heated to a temperature higher than the glass transition temperature Tg and lower than the melting point of the biodegradable polymer constituting the thread for a stent for vessels 10, so as to be deformed to a size consistent with the size of the mold frame 101. The stent 21 equipped on the mold frame 101 then is cooled, along with the mold frame 101, to a temperature lower than the glass transition temperature Tg. This affords to the stent 21 the shape memory properties so that the stent is fixed in the deformed state. The stent 21, obtained in this manner, is shape-memorized to the diameter R1 of approximately 3 to 5 mm and to the length L1 of 10 to 15 mm, as shown in FIG. 7. This size corresponds to or is larger than the diameter with which the stent is implanted in the blood vessel of the living body.

This shape-memorized stent 21 is contracted in diameter after it is dismounted from the mold frame 101. This contraction in diameter occurs as the main body portion of the main stent body 13 is deformed under a mechanical force applied from the outer perimeter of the main body portion of the main stent body 13 in the state in which the stent is cooled to a temperature lower than the glass transition temperature Tg.

Figure 12:
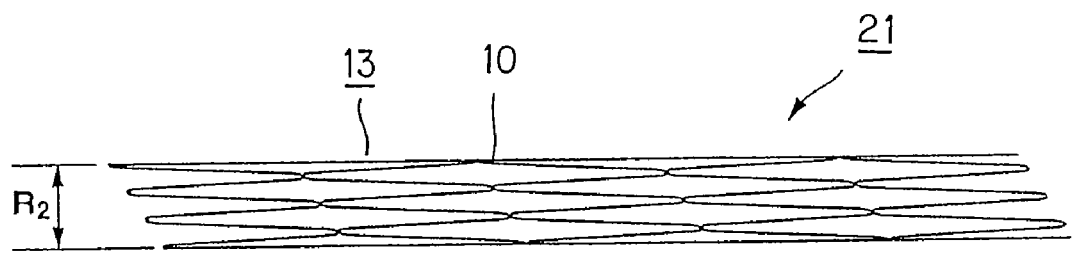
FIG. 12 is a plan view showing the state of the stent for vessels contracted in diameter.

The stent 21 is contracted in diameter by displacing the bends 14 so that the opening angle 01 of the bend 14 will be a smaller opening angle 02, as shown in FIG. 1. This diameter contraction, achieved by displacing the bends 14, is performed by deforming the bends 14 of the thread for a stent for vessels 10 cooled to a temperature lower than the glass transition temperature Tg. At this time, the stent 21 is contracted in diameter so that the stent 21 can be easily implanted in the vessel of the living body. For example, in the stent 21, shape-memorized to the diameter R1 of approximately 3 to 5 mm, the diameter is contracted to a diameter R2 of approximately 1 to 2 mm, as shown in FIG. 12.

If the stent 21, contracted in diameter by application of an external force, is heated to a temperature higher than the glass transition temperature Tg of a biodegradable polymer forming the thread for a stent for vessels 10, it is relieved of the strain afforded to the bends 14, so that the bend 14 folded to the small opening angle 02 is opened to the opening angle 01 to restore to its original shape-memorized size. That is, the stent 21 on being re-heated to a temperature higher than the glass transition temperature Tg is enlarged to its original shape-memorized size, as shown in FIG. 7.

Meanwhile, the stent 21 for the vessel, according to the present invention, is used as it is inserted into the blood vessel, such as the coronary vessel of the living body, and is enlarged in diameter to the shape-memorized state, when inserted into the blood vessel, to support its inner wall. It is noted that the thread for a stent for vessels 10, making up the stent 21 for the vessel, is formed of a biodegradable polymer, with the glass transition temperature Tg lower than 70° C., in order to restore to its original shape by the temperature equal or close to body temperature of the living body.

The stent 21, formed by the thread for a stent for vessels 10, which has the glass transition temperature Tg lower than 70° C. and which is able to restore to its original shape by the body temperature of the living body, can be heated at a temperature not producing heat damages to the blood vessel of the living body, even if it is heated for enlarging its diameter to its shape-memorized state.

With the stent for the blood vessels 21, formed using the thread for a stent for vessels 10 according to the present invention, the drug may be carried by the drug-containing layer 2 so as to be positively administered to a desired site within the blood vessel. Additionally, with use of the thread for a stent for vessels 10, with the controllable release time period, the drug may be released within the blood vessels for any desired time period following the implanting of the stent within the blood vessels.

If the stent for the blood vessels 21 is formed using the thread for a stent for vessels 10, comprised of the thread 1 as the base material and only the drug-containing layer 2 on the surface thereof, as shown in FIG. 3, a polymer layer may be formed on the surface of the main stent body 13, formed of the thread for a stent for vessels 10, bent to a tubular form, by applying a solution obtained on dissolving the biodegradable polymer of the same sort as the material making up the thread 1 as the base material. That is, if the thread 1 is formed of poly-L-lactic acid (PLLA), the biodegradable polymer layer may be formed of the same sort of poly-L-lactic acid (PLLA).

The biodegradable polymer layer, formed on the surface of the main stent body 13, may be formed by coating a biodegradable polymer solution, using a coating device, or by immersing the main stent body 13 in the biodegradable polymer solution.

Since the biodegradable polymer layer is formed on the surface of the main stent body 13, it becomes possible to suppress the amount of release of the drug from the drug-containing layer 2 as well as to control the time of drug release.

The above-described stent for blood vessels is formed of the thread for a stent for vessels 10, comprised of the thread 1 and only the drug-containing layer 2 on the surface thereof. In a similar manner, the stent for blood vessels may also be formed by the other threads for a stent for vessels 20, 30 or 40. With use of these threads 20, 30 or 40, it is possible to form stents for blood vessels exhibiting the properties owned by these threads 20, 30 and 40.

With the stents, comprised of these threads 20, 30 or 40, the solutions obtained on dissolving the biodegradable polymers of the same type as the materials making up the threads 1, 11 as the base material may be coated on the surface of the main stent body unit to provide polymer layers.

EXAMPLES

Specified examples of the thread for a stent for vessels, according to the present invention, are hereinafter explained, along with the method for manufacture thereof.

Example 1

For forming a thread for a stent for vessels, according to the present invention, a thread 1 formed of a biodegradable polymer, as a base material, is provided.

The thread 1, used here, is formed by melt-spinning pellets of poly-L-lactic acid (PLLA), using a screw extruder. The thread 1, used for forming a stent for blood vessels, implanted in a living body, in particular in a coronary artery of the human being, is a continuous length of a monofilament with a diameter of approximately 150 pm. Of course, a thread 1 formed by a multifilament, composed of plural monofilaments 1 a, unified together, may also be used.

The thread 1 provided is rinsed for removing impurities, such as dust and dirt, affixed to its surface.

The thread 1 is rinsed with ethanol and with distilled water. First, the thread 1 is injected into a washing tank charged with ethanol and agitated at ambient temperature for approximately 20 minutes. This rinsing in ethanol under agitation is carried out twice. The thread 1, rinsed with ethanol, is charged into a washing tank charged with distilled water and rinsed. The thread 1, rinsed with distilled water, is preserved for one day in a vacuum indicator for drying.

As the thread 1 is rinsed, a biodegradable polymer solution, containing a drug, configured for being coated on the surface of the thread 1, is provided. Here, Tranilast and poly-L-lactic acid are used as a drug and as a biodegradable polymer, respectively.

For forming the biodegradable polymer solution, Tranilast powders and pellets of poly-L-lactic acid of the same weight as the Tranilast powders are provided.

A suitable amount of 1,4-dioxane, as a solvent, is added into a tank charged with the pellets of poly-L-lactic acid. The resulting product is heated to 90° C. and agitated to dissolve the pellets of poly-L-lactic acid. When the solvent starts to be vaporized, the solvent is added little by little until the pellets of poly-L-lactic acid are dissolved completely.

When the pellets of poly-L-lactic acid are dissolved completely, a weight amount of the Tranilast powders is added to the reaction system and agitated. When the solvent starts to be vaporized, the solvent is added little by little until the Tranilast powders become evenly dispersed in the poly-L-lactic acid solution. The desired biodegradable polymer solution is obtained by the weighed out amount of the Tranilast powders becoming dispersed homogeneously.

The poly-L-lactic acid solution, as the Tranilast-containing biodegradable polymer solution, is coated on the surface of the rinsed thread 1.

The Tranilast-containing poly-L-lactic acid solution, to be coated on the surface of the thread 1, is mixed at a ratio of 3:1 into 1,4-dioxane, as a solvent, and agitated for dilution.

The so-diluted Tranilast-containing poly-L-lactic acid solution is applied to the surface of the thread 1, using e.g. a brush for coating. At this time, the Tranilast-containing poly-L-lactic acid solution is coated so that the thickness of the coated thread, having a diameter of approximately 150 μm, may come up to approximately 165 pm. That is, the poly-L-lactic acid solution is coated to a thickness of 7 to 8 pm. The thread 1, coated with the Tranilast-containing poly-L-lactic acid solution, is preserved for one day in a vacuum indicator for drying, whereby the solvent 1,4-dioxane is completely vaporized to yield the thread for a stent for vessels 10, on the surface of which has been formed the drug-containing layer 2, as shown in FIG. 3. At this time, the drug is contained only in poly-L4actic acid in the drug-containing layer 2.

Example 2

Another thread for a stent for vessels 10, according to the present invention, comprised of a second layer 3, which is deposited on the drug-containing layer 2, as the first layer, and which is formed only of the biodegradable polymer of the same sort as the biodegradable polymer forming the thread 1, is formed by further coating the surface of the thread 1, on the surface of which is formed only the drug-containing layer 2, with a biodegradable polymer solution.

Since the thread 1 is obtained by melt-spinning pellets of poly-L-lactic acid (PLLA) using a screw extruder, a solution of poly-L-lactic acid is used as the biodegradable polymer solution coated for forming the second layer 3.

The solution of poly-L-lactic acid is obtained on adding a suitable amount of 1,4-dioxane, as a solvent, into a tank charged with pellets of poly-L-lactic acid, and heating the resulting reaction mass to 90° C., and agitating to dissolve the pellets of poly-L-lactic acid.

The solution of poly-L-lactic acid, obtained on dissolution, is coated on the drug-containing layer 2 configured on the surface of the thread 1, using e.g. a brush for coating. The solution of poly-L4actic acid is applied at this time so that the thickness of the thread 1, having a thickness of approximately 150 pm, will be approximately 165 pm, inclusive of the thickness of the drug-containing layer 2. That is, the poly-L-lactic acid solution, forming the second layer, is coated to a thickness of 7 to 8 gm, inclusive of the thickness of drug-containing poly-L-lactic acid, forming the drug-containing layer 2. The thread 1, comprised of the drug-containing layer 2 and of the second drug layer 3, formed only of the biodegradable polymer, is preserved for one day in a vacuum indicator for drying, whereby the solvent 1,4-dioxane is completely vaporized to yield the thread for a stent for vessels 10, comprised of the drug-containing layer 2 and the second drug layer 3, formed only of the biodegradable polymer, as shown in FIG. 4.

In the foregoing, the present invention is applied to a stent for blood vessels. The present invention may, however, be extensively applied to stents implanted in other vessels in the living body.

The present invention is not limited to the above-described embodiments, explained with reference to the drawings. Instead, a variety of changes, substitutions or equivalents, as may be apparent to those skilled in the art, may be encompassed within the scope of the present invention.

INDUSTRIAL APPLICABILITY

With the thread for a stent for vessels, and the stent for vessels formed using this thread, according to the present invention, a drug-containing layer is formed by depositing a biodegradable polymer solution of the same sort as the material forming the thread, admixed with the drug, and hence the drug may be prevented from becoming detached from the thread, and may positively be carried on its surface.

In addition, drug release for a further extended period of time becomes possible by providing the drug-containing layer and by having the drug contained in the melt spun thread itself.

Moreover, since the drug may positively be carried on the thread surface, the drug can be positively administered to a target site in the living body by forming the stent for vessels with use of such thread.

Since it is possible to control the period for release of the drug contained in the drug-containing layer formed on the thread surface, the drug can be released under desirable conditions following implanting the stent for vessels in the living body.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A thread formed of a biodegradable polymer for formation of a stent, said thread being composed of a base material and at least one coating layer; wherein
   said base material and the at least one coating layer are formed of substantially the same polymer; and wherein
   said at least one coating layer is formed by coating the polymer containing a drug on said base material.

2. The thread according to claim 1 wherein said thread is a monofilament obtained by melt-spinning a biodegradable polymer using a screw extruder and on drawing results in base material.

3. The thread according to claim 1, wherein said polymer is an aliphatic polyester.

4. The thread according to claim 1, wherein said polymer is PLLA.

5. The thread according to claim 1 wherein said drug exhibits at least one of an antithromotic effect or an intimal hyperplasia suppressing effect.

6. The thread according to claim 1 wherein said drug exhibits an intimal hyperplasia suppressing effect, said drug being an immunosuppressive agent or an anticancer agent.

7. The thread according to claim 1 wherein said at least one coating layer comprises a first coating layer and a second coating layer; said first and second coating layers are formed of the same sort of the polymer as the base material; said first coating layer containing said drug and said second coating layer not containing said drug.

8. A thread formed of a biodegradable polymer for formation of a stent, said thread being composed of a base material and an at least one coating layer for coating said base material; wherein
    said base material and the at least one coating layer are formed of substantially the same polymer;
    said base material contains a drug; and wherein
    said at least one coating layer is formed by coating the polymer also containing a drug on said base material.

9. The thread according to claim 8 wherein said a thread is a monofilament obtained by melt-spinning a biodegradable polymer using a screw extruder and on drawing results in said thread.

10. The thread according to claim 8, wherein said polymer is an aliphatic polyester.

11. The thread according to claim 8 wherein said polymer is PLLA.

12. The thread according to claim 8 wherein said drug exhibits at least one of an antithrombotic effect and or an intimal hyperplasia suppressing effect.

13. The thread according to claim 8 wherein said drug exhibits an intimal hyperplasia suppressing effect, and said drug is an immunosuppressive agent or an anticancer effect.

14. The thread according to claim 8 wherein said at least one coating layer comprises a first coating layer and a second coating layer; said first and second coating layers are formed of the same sort of the polymer as the base material; said first layer containing a drug and said second layer not containing a drug.

15. A stent composed of a thread formed of a biodegradable polymer for formation of a stent, said thread being composed of a base material and an at least one coating layer for coating said base material; wherein
    said base material and the at least one coating material are formed of substantially the same polymer; and wherein
    said at least one coating layer is formed by coating the polymer containing a drug and is formed by coating on said base material.

16. A stent composed of a thread formed of a biodegradable polymer for formation of a stent, said thread being composed of a base material and an at least one coating layer for coating said base material; wherein
    said base material and the coating layer are formed of substantially the same polymer;
    said base material contains a drug; and wherein
    said at least one coating layer is formed by coating the polymer also containing a drug on said base material.

* * * * *